United States Patent [19]

Franseen et al.

[11] Patent Number: 5,443,384
[45] Date of Patent: Aug. 22, 1995

[54] ORTHODONTIC ASSEMBLY AND METHOD

[75] Inventors: Steven A. Franseen, Denver; David E. Watt, Nederland, both of Colo.; William J. Clark, Lundin Links, Scotland

[73] Assignee: RMO, Inc., Denver, Colo.

[21] Appl. No.: 235,176

[22] Filed: Apr. 29, 1994

[51] Int. Cl.$^6$ ............................................. A61C 3/00
[52] U.S. Cl. ........................................ 433/18; 433/19; 433/24
[58] Field of Search ............... 433/5, 6, 7, 18, 19, 433/24, 215

[56] References Cited

U.S. PATENT DOCUMENTS

| | | |
|---|---|---|
| 1,137,298 | 4/1915 | Walker . |
| 1,142,467 | 6/1915 | Walker . |
| 1,217,374 | 2/1917 | Walker . |
| 2,243,377 | 5/1941 | Haller ........................... 32/8 |
| 2,334,894 | 11/1943 | Atkinson ..................... 32/14 |
| 2,473,515 | 6/1949 | Egger ............................ 32/8 |
| 2,479,780 | 8/1949 | Remensnyder ............ 32/14 |
| 2,708,314 | 5/1955 | Schwartz ..................... 32/2 |
| 3,043,005 | 7/1962 | Morris ........................... 32/2 |
| 3,762,050 | 10/1973 | Dal Pont .................... 32/14 A |
| 3,820,242 | 6/1974 | Haskins ...................... 32/14 A |
| 4,245,986 | 1/1981 | Andrews ..................... 433/5 |
| 4,354,834 | 10/1982 | Wilson ........................ 433/21 |
| 4,375,355 | 3/1983 | Dahan ......................... 433/5 |
| 4,375,962 | 3/1983 | Dewoskin .................... 433/5 |
| 4,439,149 | 3/1984 | Devincenzo ................ 433/6 |
| 4,509,918 | 4/1985 | Clark ........................... 433/5 |
| 4,619,609 | 10/1986 | Clark ........................... 433/6 |
| 4,671,767 | 6/1987 | Blechman et al. ......... 433/19 |
| 4,871,310 | 10/1989 | Vardimon .................. 433/19 |
| 5,242,304 | 9/1993 | Truak et al. ................ 433/7 X |
| 5,324,196 | 6/1994 | Magill ......................... 433/19 |

FOREIGN PATENT DOCUMENTS

1438759  11/1988  U.S.S.R. ................... 433/19

Primary Examiner—Nicholas D. Lucchesi
Attorney, Agent, or Firm—Sheridan Ross & McIntosh

[57] ABSTRACT

An improved orthodontic assembly and method is disclosed. The orthodontic assembly includes opposing complementary bite blocks separately mountable utilizing separate mounting assemblies. Preferably, the mounting assembly for at least one of the upper or lower bite blocks of each upper/lower set allows for selective antero-posterior positioning. Each bite block preferably comprises a preformed portion and a formable layer that can be adapted to an occlusal surface for flush mounting thereupon.

19 Claims, 6 Drawing Sheets

MANDIBULAR

MAXILLARY

ORTHODONTIC ASSEMBLY AND METHOD

FIELD OF THE INVENTION

This invention relates to an improved orthodontic assembly and method for fixed or fixed/removable use, and more particularly, to an assembly and method comprising separate and readily mountable opposing bite block arrangements for enhancing maxillary/mandibular positioning.

BACKGROUND OF THE INVENTION

Increasingly, orthodontic practitioners are addressing malocclusion and other undesired conditions by initiating orthopedic treatment techniques during patient adolescence or even prior thereto so as to benefit from growth potentials. Such techniques include the utilization of unitary, custom-made appliances which, for example, induce maxillary/mandibular alignment and selectively retard/augment maxillary/mandibular growth.

Figure 1:
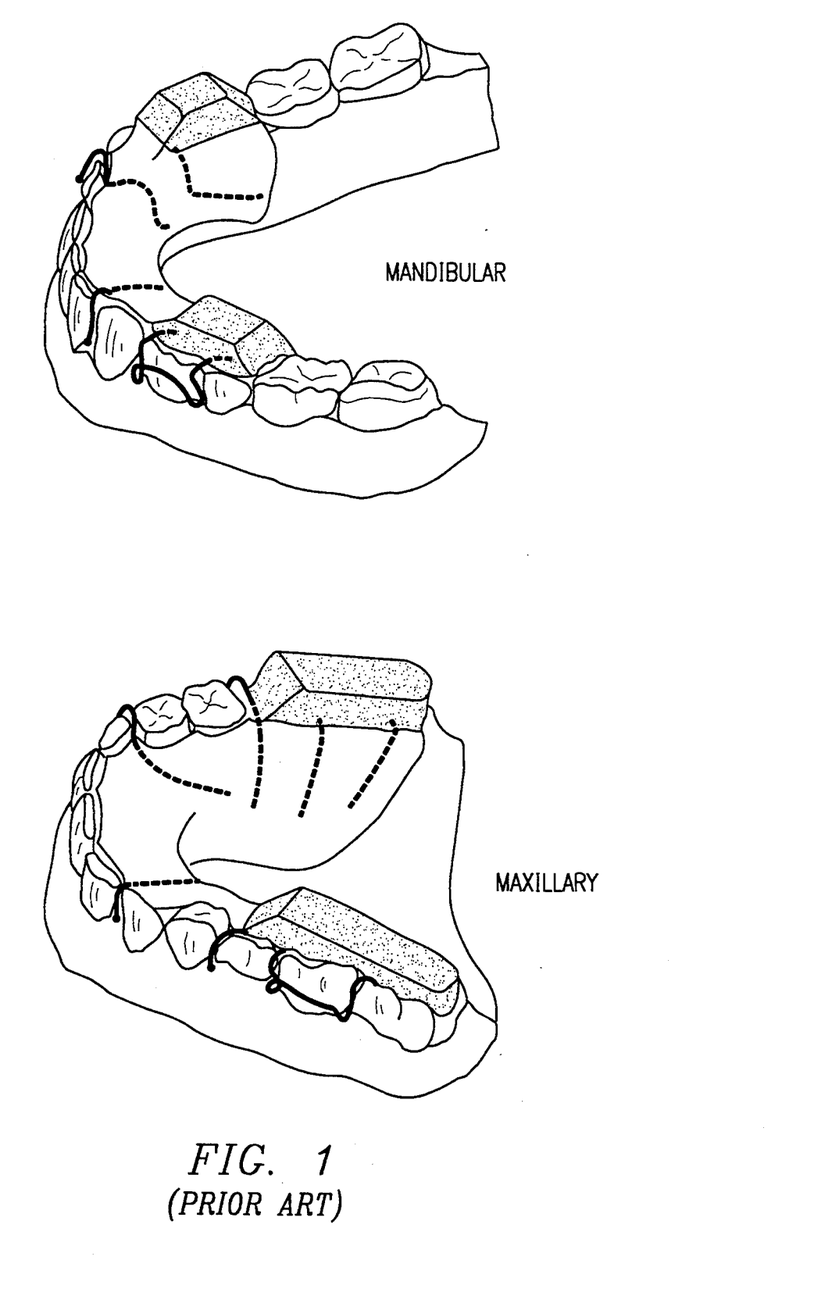
FIG. 1 illustrates prior art unitary maxillary and mandibular bite block appliances.

One such type of appliance is based on the disclosure of U.S. Pat. No. 4,619,609. Briefly, the '609 patent describes an appliance having two maxillary bite blocks posteriorly positioned on each side of the mouth and an appliance having two mandibular bite blocks positioned in opposing relation to the maxillary bite blocks. The upper and lower bite blocks are provided with complimentary inclined surfaces wherein, upon mouth closure, a camming effect between the inclined surfaces is achieved so as to promote, for example, forward projection of the mandible or maxilla. As commercialized, each appliance comprises a unitary palatal molding for removable usage. More specifically, and as illustrated in FIG. 1, the unitary maxillary and mandibular appliances each include the two corresponding bite blocks molded into an interconnecting structure which extends therebetween, most typically with additional integrally-molded, clasp-like extensions for removable retention on a patient's teeth. In this regard, it should be appreciated that the manufacture of such unitary maxillary and mandibular appliances has necessarily required practitioners to obtain impressions from which study models can be produced on a patient-specific basis. Such impressions or study models are then provided to third-party orthodontic/dental laboratory production facilities having the necessary equipment, expertise, etc., to mold the unitary, customized products.

SUMMARY OF THE INVENTION

Accordingly, an objective of the present invention is to provide an orthodontic bite block assembly that simplifies production requirements. A related objective is to provide an orthodontic bite block assembly that utilizes preformed bite blocks that can be separately and readily customized and orally disposed without a unitary molded structure extending between the left and right sides of the maxilla or mandible.

Another object of the present invention is to provide an orthodontic bite block assembly which may be utilized in either a fixed or fixed/removable treatment mode.

An additional object of the present invention is to provide a mounting assembly that allows for convenient and adjustable mounting of orthodontic components relative to a reference position, including specifically selective antero-posterior positioning of orthodontic bite blocks.

In one aspect of the present invention, an orthodontic assembly is provided comprising separate sets of complementary upper and lower bite blocks having complementary angled camming surfaces and corresponding block mounting assemblies for separate mounting in either a fixed (e.g., adhesively interconnected to the teeth and therefore not readily removable) or fixed/removable (e.g., mechanically interconnected to the teeth in a manner which is not readily removable by a patient, but is by a practitioner) manner. Each bite block preferably includes a preformed portion that includes the angled surface thereof and a formable layer adjoined/readily adjoinable thereto and being conformable to flushly engage an occlusal surface upon mounting. Each mounting assembly includes block connection means connected to the corresponding block, a tooth attachment means that is selectively secured directly to a tooth, and interconnection means for selectively interconnecting the tooth attachment means and block connection means.

The block connection means corresponding with at least one of the upper and lower bite blocks of each set preferably includes first and second portions connected to and extending from opposing sides of the bite block for positioning adjacent to lingual and buccal tooth surfaces, respectively. At least the first portion preferably extends longitudinally (i.e., antero-posteriorly relative to the block), and most preferably in a reward direction. The first and second extending portions are preferably integrally adjoined by an intermediate portion therebetween, such intermediate portion being anchored within the preferred preformed portion of the corresponding bite block (e.g., preferably within the most forward ⅓ portion of the antero-posterior length of the bite block).

The interconnection means of the mounting assembly corresponding with at least one of the upper and lower bite blocks of each upper/lower set preferably includes a separate lingual connection means for slidably and horizontally engaging the first extending portion of the corresponding block connection means, thereby allowing for adjustable, interconnected antero-posterior positioning of at least one bite block of each upper/lower set at a plurality of locations along a continuum relative to a known reference position (e.g., the corresponding tooth attachment means). Further, the interconnection means may also include a separate buccal connection means for slidably engaging, preferably horizontally, the second extending portion of the block connection means, so as to further enhance antero-posterior block positioning and lateral stability.

More generally in this regard, an important aspect of the present invention is to provide a mounting assembly that permits orthodontic components (i.e., for present purposes, the above-described bite blocks) to be selectively positioned at a plurality of antero-posteriorly offset (i.e., forwardly/rearwardly offset) locations relative to a given reference position. By way of example here, such plurality of offset locations may be within a plane generally coincident with an occlusal plane, thereby allowing for separate and selective forward/rearward positioning of at least one of the upper or lower described bite blocks of each set on a per-patient basis so as to achieve the desired camming interface of the complimentary angled surfaces.

Preferably, the interconnection means of each mounting assembly that provides selective antero-posterior positioning includes a dual connection member having a first mating portion for slidable mating engagement with one of the extending portions of the block connection means, and a second mating portion, oriented transversely to said first mating portion, for mating engagement with a complimentary member interconnected to the tooth attachment means. In this regard, it is preferred that such complimentary member comprise a female means (e.g., one or more vertical tubes) fixedly connected to the tooth attachment means (e.g., a band), and that the second mating portion of the dual connection member include a male means (e.g., one or more vertical posts) for easy vertical insertion into the female means of the complimentary member. The first mating portion of the dual connection member may comprise a female means (e.g., a horizontal tube) for slidably receiving one of the extending portions of the block connection means. Alternatively, the first mating portion may comprise a male means (e.g., a horizontal wire end section) for slidable positioning within a female tubular end of the block connection means.

Preferably, the above-described dual connection member and complementary member of the interconnection means are lingually disposed for interconnection with a first extending portion of the block connection means. In this regard, the interconnection means of each mounting assembly that provides selective antero-posterior positioning may also comprise a buccally disposed member for slidably engaging the second extending portion of the block connection means. Preferably, the second engaging portion also extends longitudinally from the block (e.g., rearwardly) and the buccally disposed member horizontally and slidably engages the second portion. As will be appreciated then, the above-described mounting assembly most preferably provides both lingual/buccal support and selective slidable, antero-posterior positioning for an orthodontic component relative to a given tooth or other reference position.

As utilized in the above-described bite block assembly, the mounting assemblies for both lower bite blocks and/or for both upper bite blocks may further advantageously comprise an adjoining means for slidably engaging an adjoining member disposed between the two lower bite blocks and/or two upper bite blocks so as to achieve coordinated right side/left side response to the bite block assemblies. Such arrangement may include, for example a lingual arch device slidably received at each end by a second horizontal tube interconnected to the lingually disposed dual connection member or first extending portion of each corresponding mounting assembly.

Relatedly, it has been recognized that, in addition to the described bite block arrangements, the described mounting assembly is apt for use in the independent mounting of various active lingual arch devices. For example, it has been recognized that a dual connection member and tooth attachment means having a lingually disposed complementary member (as described above) can be readily mounted on each side of the mandible so as to slidably receive an active lingual arch device therebetween. In this regard, and in yet another inventive aspect, for example, it has been discovered that each end of a lingual archwire can be slidably received by a horizontal tube (e.g., each being interconnected to a corresponding dual connection member as described above) with a resilient sheath positioned on the archwire being compressed and retained between the two dual connection members. In such an arrangement, the mounting assembly facilitates mounting and allows the lingual archwire to slidably pass through the dual connection members as mandible growth is augmented in response to the expansion force applied to the lingual aspect of the lower teeth by the resilient sheath.

Other similar applications and extensions of the disclosed mounting assembly are possible. In this regard, it should also be noted that the preferred bite block assembly described hereinabove may be supplemented by plural additional tubes (e.g., horizontal, angulated or vertical) interconnected to the mounting assembly (e.g., to the dual connection members) to accommodate selective mounting of various additional orthodontic components.

In a further aspect of the present invention, a method of providing an orthodontic assembly for use is disclosed. In this regard, the utilization of preformed bite blocks, preferably having the described block connection means anchored therewithin, allows for the supply of a plurality of preformed blocks of different sizes/angled surface dimensions from which one may be readily selected for a given treatment regime. The blocks may be supplied with the formable layer already adjoined thereto or the formable layer may be applied to the preformed blocks by the practitioner/technician. The formable layer may comprise a material preferably selected from the following group: thermoplastic elastomers, chemically curable compositions (e.g., a dimethacrylate paste activated by benzoyl peroxide-amine or a methyl methacrylate composition), light-curable compositions (e.g., dimethacrylate paste activated by camphor quinone), thermoplastics and thermoset plastics. In the preadjoined embodiment, the formable layer most preferably comprises a thermoplastic elastomer, e.g., a thermoplastic urethane (i.e., polyester-urethane, polyether-urethane or caproester urethane) or copolyether-ester. When a thermoplastic elastomer is utilized in the formable layer, the bite block should be heated to between about 100° F. to 210° F. to soften the preformed portion prior to forming. In the embodiment wherein the formable layer is applied by the practitioner/technician, the formable layer most preferably comprises a light-curable composition which will typically already be in a softened state (i.e., as maintained in inventory). When a light-curable composition is utilized, it is preferred that the preformed block(s) be transparent (e.g., preferably allowing at least about 80% or more of incident light to pass therethrough) and readily bondable to and chemically compatible with the light-curable composition. By way of example, acrylic, polycarbonate and polysulfone materials appear to be particularly apt in this regard. Preferably, prior to forming the formable layer, a separating medium (e.g., vaseline, soap, etc.) is applied to the patient's teeth or study model to facilitate later removal.

To form the formable layer, the bite block is positioned in a desired location on and relative to the occlusal surface of the patient's teeth or study model. The formable layer is then conformed to the shape of the occlusal surface by the manual application of finger pressure to the block. Subsequently, the formable layer is allowed to sufficiently harden on such occlusal surface so that the occlusal surface topography is maintained in the formable layer. For example, such hardening occurs with the cooling of a thermoplastic elastomer formable layer, and upon visible light exposure when a light-curable composition is employed for the formable layer. In the latter regard, a high-intensity visible light can be used to expedite hardening and the advantage of utilizing a transparent preformed block can be readily appreciated. After initial hardening, the bite block can thus be removed to complete the hardening process (e.g., by further exposure to high-intensity light for light curable compositions). Each block may then be mounted on and interconnected to the patient's teeth, preferably utilizing the above-described mounting assembly, and for fixed arrangements, utilizing an appropriate adhesive. Alternatively, the block may be interconnected in a fixed arrangement utilizing only an adhesive.

DETAILED DESCRIPTION

Figure 2:
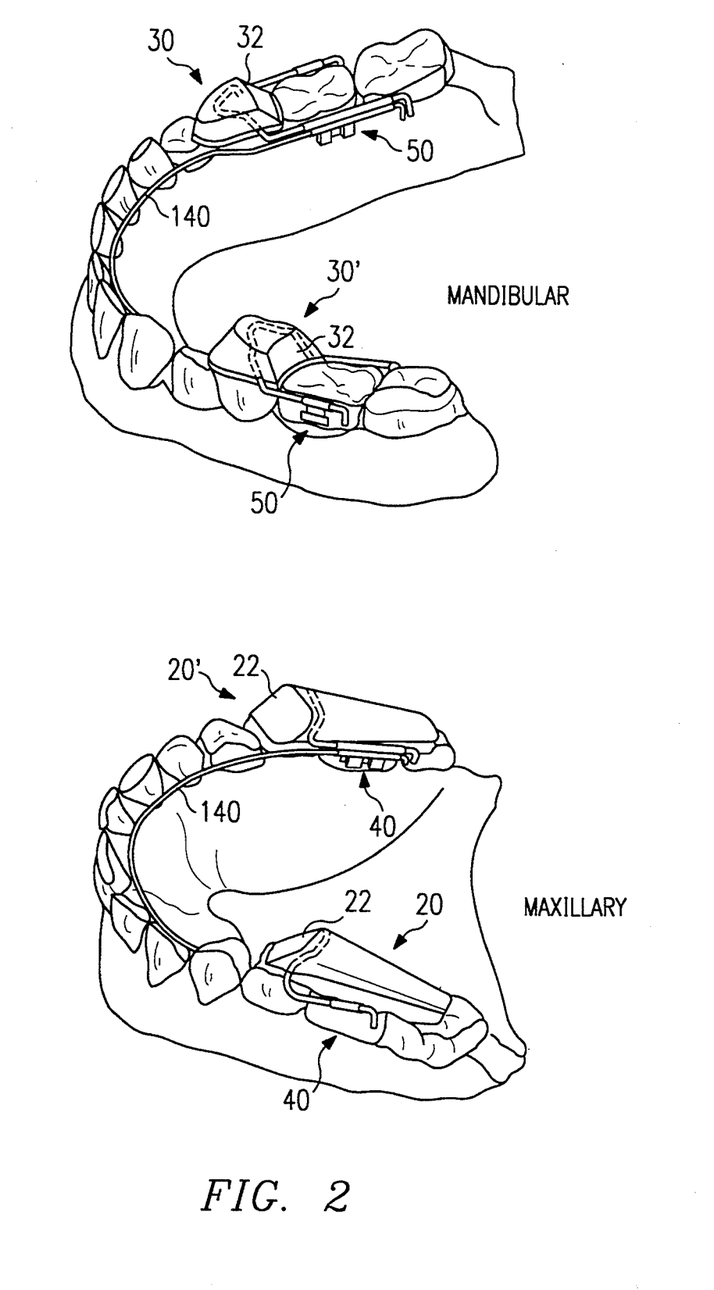
FIG. 2 illustrates one embodiment of the present invention as disposed for use.
Figure 3:
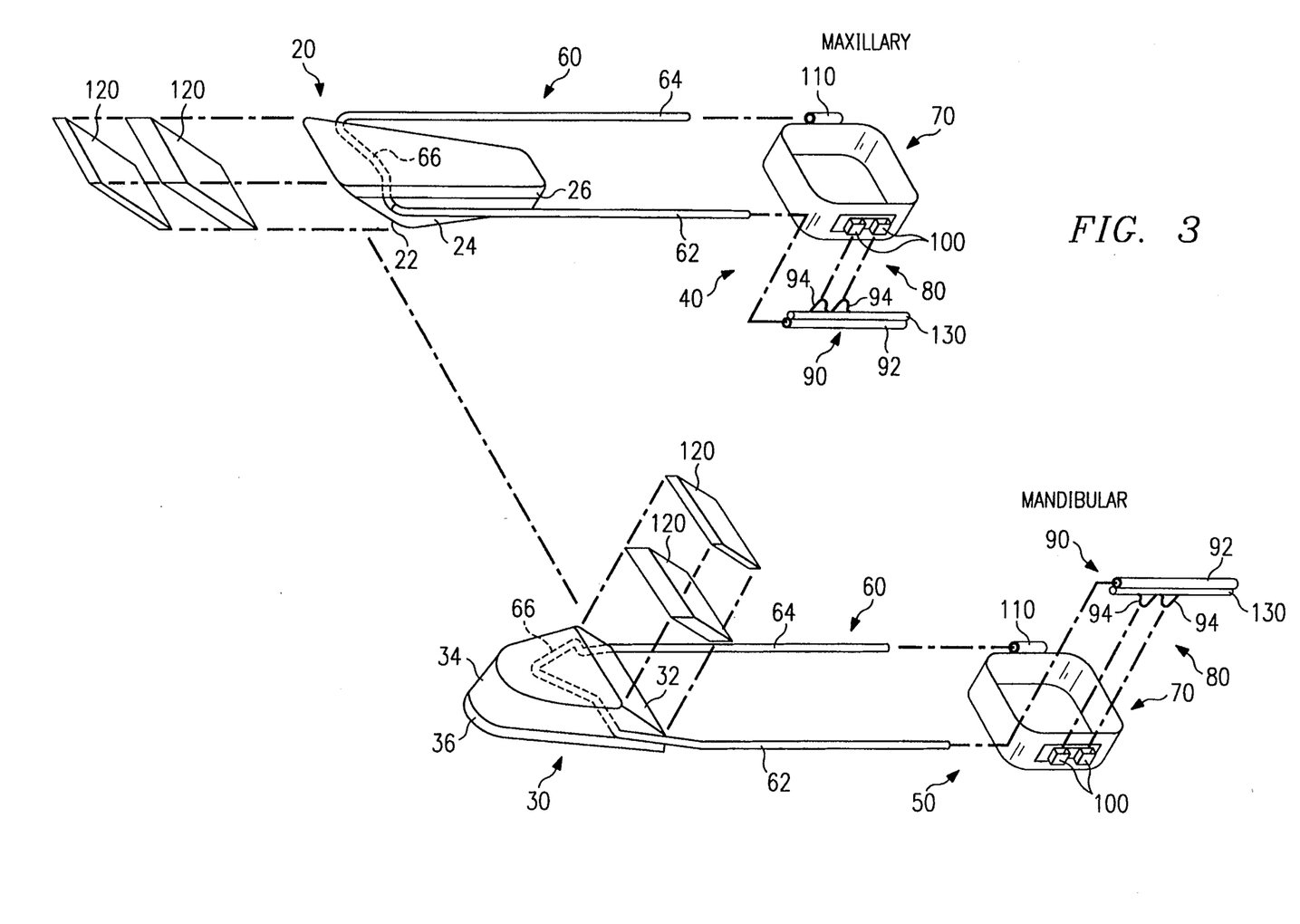
FIG. 3 is an exploded illustration of one embodiment of the present invention, the upper and lower bite block assemblies being oriented in their use positions.

In the embodiment illustrated in FIG. 2, two upper (i.e., maxillary) bite blocks 20,20', and two lower (i.e., mandibular) bite blocks 30,30' are disposed utilizing upper (i.e., maxillary) and lower (i.e., mandibular) mounting assemblies 40,50 such that the corresponding angled surfaces 22 and 32 will engage in a camming fashion with mouth closure. As best shown in FIG. 3, upper and lower mounting assemblies 40,50 each generally comprise block connection means 60, tooth attachment means 70, and interconnection means 80 as will be further described.

Each of the bite blocks 20,20' and 30,30' include a preformed portion 24,34 and formable portion 26,36, respectively. The preformed portion 24,34 should be constructed to provide a solid structure with angled surfaces 22,32 being wear resistant to accommodate the desired camming therebetween. For example, preformed portion 24,34 may comprise a unitary molded acrylic. Alternatively, and without limitation, preformed portion 24,34 may comprise a metal member defining the angled surface 22,33 and having extensions anchored, or molded, within a filler material.

As illustrated, the angled surfaces 22,32 of the bite blocks 20,20',30, 30' are provided to inhibit maxillary growth and encourage mandibular growth. Preferably, such surfaces are disposed at an angle of between about 45° to 75° relative to the occlusal plane. Alternatively, it should be appreciated that the angled surface orientation may be reversed so as to promote maxillary growth and inhibit mandibular growth. Further, while not shown, the bite blocks 20,20',30, 30' can be provided with "locking mating portions" adjacent to the occlusal interface of angled surfaces 22,32 such that, after a desired degree of camming travel has occurred, the upper and lower bite blocks 20,20' and 30,30' will not progress further.

Bite blocks 20,20',30, 30' are each connected to corresponding block connection means 60 which each comprise a rearwardly extending first portion 62 and second portion 64. The first extending portion 62 and second extending portion 64 are integrally adjoined by an intermediate portion 66 disposed within the preformed portion 24,34 of the bite blocks 20,20' and 30,30' (e.g., by insert or injection molding). In this regard, the intermediate portion 66 of block connection means 60 is disposed in the forward region of upper blocks 20,20' (e.g., in the most forward ⅓ portion), thereby allowing for removal of rearward portions of blocks 20,20' during use.

Each mounting assembly 40 further comprises a tooth attachment means 70 selectively attachable to a tooth and interconnection means 80 for selectively interconnecting the tooth attachment means 70 and said first extending portion 62 and second extending portion 64 of the block connection means 60. As illustrated, the tooth attachment means 70 may be in the form of bands sized and positioned about the corresponding teeth to provide a fixed connection therebetween.

The interconnection means 80 may include a dual connection member 90. In the embodiment of FIG. 3, dual connection member 90 includes a cylindrical tube portion 92 and male members 94 extending laterally therefrom. Tube portion 92 is sized for slidingly receiving therethrough first extending portion 62 of the block connection means 60. Interconnection means 80 may further comprise female members 100 affixed to a lingually disposed surface of the tooth attachment means 70 and otherwise adapted for receiving male members 94 of the dual connection member 90. Interconnection means 80 may further comprise a cylindrical tube 110 fixedly connected to a buccally disposed surface of tooth attachment means 70 for sliding receipt of the second extending portion 64 of block connection means 60 therethrough.

Figure 6:
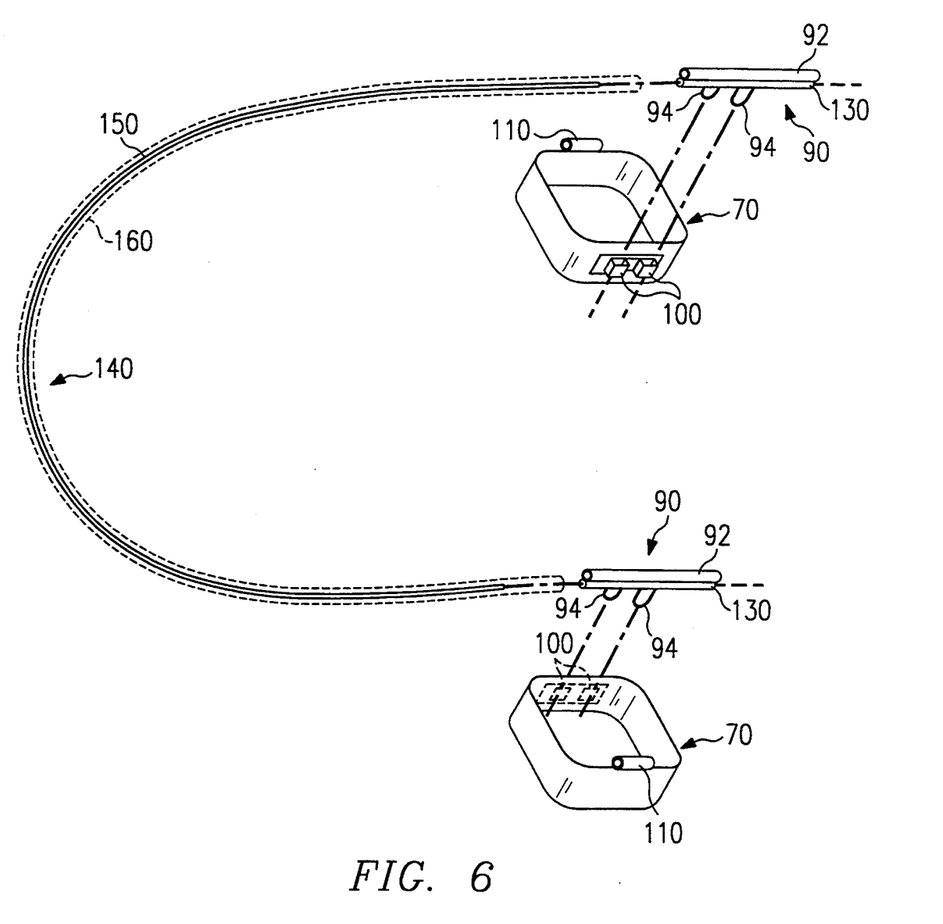
FIG. 6 is an exploded illustration of portions of the two lower bite block mounting assemblies per the embodiment of FIG. 3, with a novel active lingual arch device disclosed for slidable engagement with such mounting assemblies.

As illustrated in FIGS. 2, 3 and 6, the dual connection member 90 further comprises a second horizontally disposed tube 130 for slidably receiving a lingual arch device 140 therethrough. Such lingual arch device 140 may simply comprise a lingual arch wire for coordinating right side/left side response to the bite blocks 20,20'30,30' and may further comprise an active lingual arch device. In the latter regard, FIG. 6 illustrates a novel active lingual arch device comprising lingual arch wire 150 and resilient outer sheath 160 (shown in dotted lines). In use, outer sheath 160 is partially compressed between right and left dual connection members 90 so as to impart an active antero-posteriorly oriented force on the lingual aspect of the mandibular teeth.

Figure 4:
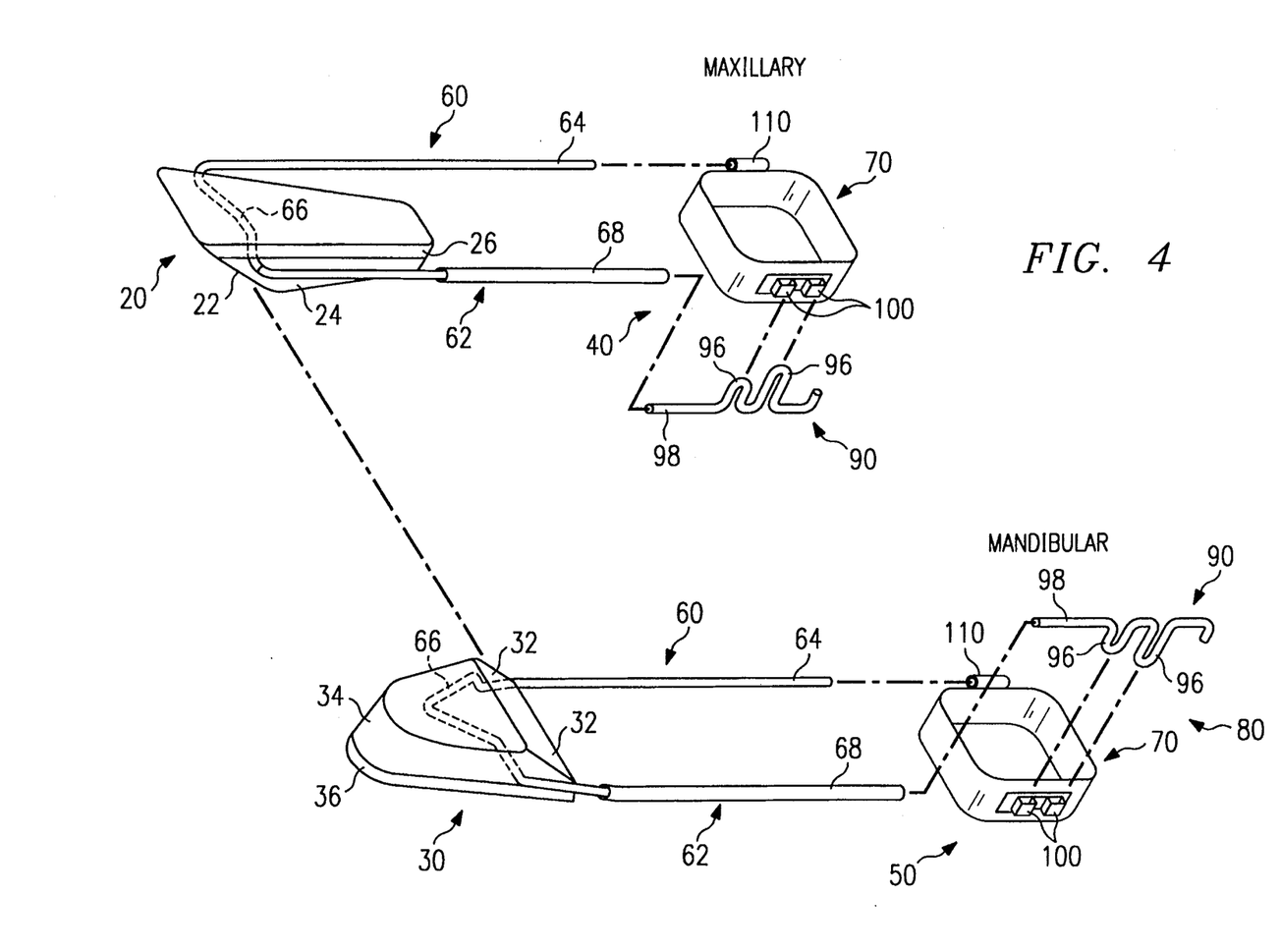
FIG. 4 is an exploded illustration of another embodiment of the present invention, the upper and lower bite block assemblies being oriented in their use positions.

In the embodiment shown in FIG. 4, dual connection member 90 is defined by a wire shaped to provide male members 96 and sized so that end portion 98 thereof may be slidably inserted into a tubular end portion 68 provided on first extending portion 62. Alternatively, the entirety of first extending portion 62 may be of tubular construction. Slidable engagement between end portion 98 and first extending portion 62 allows for selective antero-posterior positioning as previously described.

Figure 5:
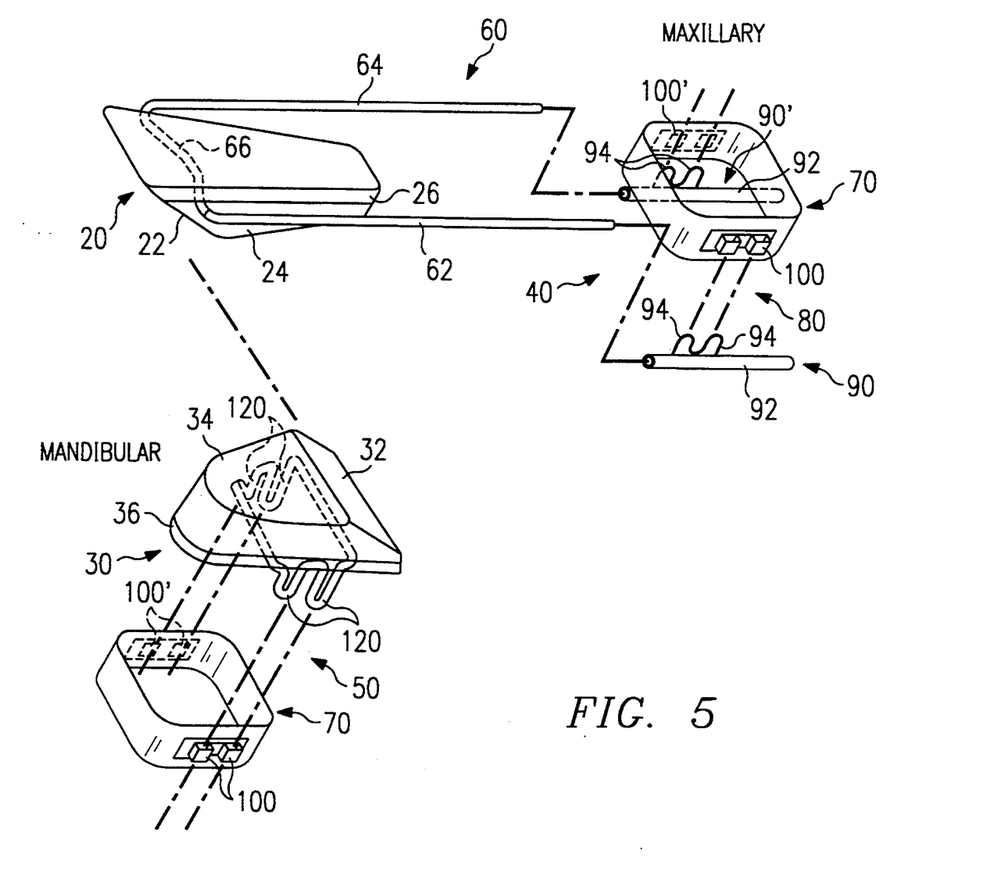
FIG. 5 is an exploded illustration of yet another embodiment of the present invention, the upper and lower bite block assemblies being oriented in their use positions.

In the embodiment of FIG. 5, lower block 30 is illustrated having lingual/buccal male posts 120 extending from each side for direct insertion into corresponding lingual/buccal female member 100,100' provided on tooth attachment means 70. As such, relative anteroposterior positioning of upper block 20 and lower block 30 is provided solely by the mounting assembly 40 of the upper block 20. In this regard, an added dual connection member 90' and bucally disposed female member 100' may be employed for interconnection with the second extending portion 64 of block connection means 60.

As will be appreciated, the various features illustrated with respect to the embodiment of FIGS. 3–5 may be utilized in many different combinations to achieve the desired effectiveness and utility.

In use of the illustrated embodiments, tooth attachment means 70 is typically mounted on the upper and lower first molars (or on deciduous molars in pre-adolescent patients).

Bite blocks 20,20',30, 30' are then prepared for forming. In the illustrated embodiment, and by way of example, formable portion 26,36 may comprise a thermoplastic elastomer such as copolyether-ester. Such a material is available, for example, under the name "HYDROPLASTIC" from TAK Systems of Wareham, Mass. In such embodiment, the formable blocks 20,20',30,30' are exposed to an elevated temperature (e.g., about 100° F. to 210° F.) to soften formable portion 26,36.

Alternatively, it should be appreciated that formable portion 26,36 may be applied to preformed portion 24,34 just prior to forming. For such embodiments, and in addition to thermoplastic elastomers, the formable portion 26,36 may comprise materials applied in a formable state such as a light-curable composition, chemically-curable composition, thermoplastic or thermoset plastic. When a chemically-curable composition is utilized (e.g., dimethacrylate paste activated by benzoyl peroxide-amine or a methyl methacrylate composition), the activator should first be applied (e.g. by brushing) to the occlusal surface and perhaps the tooth facing surface of the preformed block portions 24,24',34, 34'.

With the formable portion 26,36 in a formable state, bite blocks 20,20',30, 30' can then be positioned relative to the corresponding desired occlusal tooth surface and manually pressed thereupon such that formable portion 26,36 conforms to the shape of the corresponding occlusal surface. By way of example, in the use of the embodiments of FIGS. 3 and 4 practitioners may find it useful to insert the second extending portion 64 of block connection means 60 into the horizontal tube 110 connected to the tooth attachment means 70 so as to provide lateral stability, then pivot and slide the bite block into the desired position for forming. In this regard, the dual connection member 90 may also be slidably positioned on the first extending portion 62 of the block connection means 60 and rotatably inserted into vertical tubes 100 during positioning.

Following formation of formable portion 26,36, formable portion 26,36 should be allowed to at least partially harden. Specifically, formable portion 26,36 should be allowed to harden sufficiently in situ to maintain the desired tooth interface shape. The blocks 20,20'30,30' may then be removed to complete the hardening. In this regard, when a light-curable composition is utilized for formable portion 26,36, the beam of a high-intensity visible light can be directed into the formable portion 26,36 and through preformed portions 24,34 if a transparent material (e.g., acrylic, polycarbonate or polysulfone) is used therefor, both in situ and following removal to expedite hardening.

For treatment, the assembly can be readily positioned within the patient's mouth by sliding second extending portion 64 into horizontal tube 110 to the desired location, slidingly engaging dual connection member 90 on first extending portion 62 and then inserting male members 94 into the female members 100. As can be appreciated, the relative slidability and rotatability between second extending portion 64 and horizontal tube 110, as well as between dual connection member 90 and first extending portion 62, allows for readily mounting of bite blocks 20,20' and/or 30,30' at a plurality of locations relative to a reference position.

For fixed arrangements, an appropriate adhesive may be applied to the tooth adjoining surface of the formable portion 26,36 after forming and/or to the occlusal tooth surface. By way of example, such adhesive may be selected from the group comprising: glass ionomer, light curing ionomer, luting cement, "Black Copper" cement, deposit bonding resins, zinc oxide cement, alumina EBA cement, veneer resins and various methyl methacrylate compositions.

As will be appreciated, the opposing angled surfaces 22,32 of upper and lower bite blocks 20,20' and 30,30' will engage upon mouth closure, and the desired maxillary/mandibular positioning and growth augmentation will be promoted. As this is achieved, it may be desirable to further extend the camming surfaces of upper bite blocks 20,20' and/or lower blocks 30,30' by adhering additional spacers 120 thereto. Alternatively, upper bite blocks 20,20' and/or 30,30' may be removed and formable layer 26 and/or 36 may be resoftened (e.g., when a thermoplastic elastomer material is employed) and/or a new layer applied, followed by reforming the formable layer 26 and/or 36 and remounting of the assembly.

In situations involving young patients, it may be desirous to promote or facilitate eruption of the lower first and second molars. To facilitate the same, the practitioner can readily remove the reward portion of the upper bite block 20,20' by trimming the same so as to create additional space for eruption of the lower molars. In these applications, the use of the embodiment of FIG. 5 may prove particularly effective.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. An orthodontic assembly comprising:
   a first lower bite block having an angled cam surface;
   a first upper bite block having an angled cam surface complimentary to the cam surface of said first lower bite block; and a mounting assembly for separately mounting at least one of said first lower bite block and first upper bite block, including:
attachment means adapted to be fixedly attached directly to a tooth;
block connection means connected to said at least one of said blocks; and,
interconnection means for selectively interconnecting said attachment means and said block connection means.

2. An orthodontic assembly as recited in claim 1, said interconnection means comprising:
a first male member interconnected to one of said attachment means and block connection means; and,
a first female member interconnected to the other of said attachment means and block connection means for receiving said first male member.

3. An orthodontic assembly as recited in claim 2, wherein one of said first male member and first female member slidably engages said one of said attachment means and block connection means.

4. An orthodontic assembly as recited in claim 3, wherein the other of said first male member and said first female member is fixedly connected to the other of said attachment means and block connection means.

5. An orthodontic assembly as recited in claim 3, wherein said one of said first male member and first female member is axially and rotatably positionable relative to said one of said attachment means and block connection means.

6. An orthodontic assembly as recited in claim 1, said block connection means including:
a first extending portion connected to a first side of said at least one of said blocks, said first extending portion being positionable adjacent to a lingual surface of said tooth; and
a second extending portion connected to a second side of said at least one of said blocks, said second extending portion being positionable adjacent to a buccal surface of said tooth.

7. An orthodontic assembly as recited in claim 6, said interconnection means comprising:
first connection means for selective interconnection of said first extending portion of said block connection means and a lingually disposed portion of said attachment means;
second connection means for selective interconnection of said second extending portion of said block connection means and a buccally disposed portion of said attachment means.

8. An orthodontic assembly as recited in claim 7, wherein said first connection means and first extending portion are disposed for horizontal mating and relative slidable engagement.

9. An orthodontic assembly as recited in claim 7, wherein said first connection means comprises:
at least one vertically oriented female member fixedly connected to said lingually disposed portion of said attachment means; and
a dual connection member having at least one vertically oriented male member selectively positionable within said one female member, and an interconnected, horizontally oriented portion for selective horizontal mating and relative slidable engagement with said first extending portion of said block connection means.

10. An orthodontic assembly as recited in claim 9, wherein said second connection means comprises:
a horizontally oriented member fixedly interconnected with said buccal portion of said attachment means for selective horizontal mating and relative slidable engagement with said second end portion of said block connection means.

11. An orthodontic assembly as recited in claim 10 wherein said horizontally oriented portion includes a first horizontal tube.

12. An orthodontic assembly as recited in claim 11, wherein:
said horizontally oriented portion further comprises a second horizontal tube.

13. An orthodontic assembly as recited in claim 6, wherein said at least one bite block is selectively positionable at a plurality of locations relative to said tooth.

14. An orthodontic assembly as recited in claim 6, said first and second extending portions being integrally interconnected by an intermediate portion therebetween, said intermediate portion being positioned within said at least one of said blocks.

15. An orthodontic assembly as recited in claim 1, said at least one of said blocks comprising:
a preformed portion having a tooth facing surface; and
a formable layer selectively adjoined to said tooth facing surface and being formable to flushly engage an occlusal surface of said tooth.

16. An orthodontic assembly as recited in claim 1, further comprising:
at least one spacer selectively adjoinable to the cam surface of at least one of said first lower bite block and first upper bite block.

17. A method for providing an orthodontic assembly for use on one or more of a patient's teeth, comprising the steps of:
supplying at least a first preformed lower bite block and at least a first preformed upper bite block, said blocks having complementary angled cam surfaces, and each of said blocks having a tooth facing surface;
providing a layer of a formable material to the tooth facing surface of at least one of said first lower bite block and first upper bite block;
positioning said at least one of said blocks in a desired location on and relative to an occlusal surface of one of either said patient's teeth or a patient's study model thereof;
forming an outer surface of said formable material to the shape of said occlusal surface by applying force to said one block;
at least partially hardening said formable material on said occlusal surface;
removing said at least one of said blocks from said occlusal surface; and
interconnecting said at least one of said blocks to said teeth.

18. A method for providing an orthodontic assembly for use, as recited in claim 17, wherein:
said formable material is selected from the group comprising:
thermoplastic elastomer materials, light-curable compositions, chemically-curable compositions, thermoplastics and thermoset plastics.

19. A method for providing an orthodontic assembly for use, as recited in claim 17, wherein:
said at least one of said bite blocks is transparent;
said formable material comprises a light-curable composition; and
said partial hardening step includes:
exposing said at least one of said bite blocks and formable material to visible light.

* * * * *